United States Patent [19]

Ranawat et al.

[11] Patent Number: 4,714,476
[45] Date of Patent: Dec. 22, 1987

[54] WRIST JOINT PROSTHESIS

[75] Inventors: Chitranjan S. Ranawat, Alpine, N.J.; Lee R. Straub, New York; Allan E. Inglis, Rye, both of N.Y.; Albert H. Burstein, Stamford, Conn.

[73] Assignee: New York Society for the Relief of the Ruptured and Crippled, New York, N.Y.

[21] Appl. No.: 6,984

[22] Filed: Jan. 27, 1987

[51] Int. Cl.$^4$ .............................................. A61F 2/42
[52] U.S. Cl. ..................................................... 623/21
[58] Field of Search ............................. 623/20, 21, 18

[56] References Cited

U.S. PATENT DOCUMENTS

| | | |
|---|---|---|
| 4,229,840 | 10/1980 | Gristina . |
| 4,229,841 | 10/1980 | Youm et al. . |
| 4,301,553 | 11/1981 | Noiles ................................. 623/20 |
| 4,307,473 | 12/1981 | Weber ................................. 623/21 |
| 4,352,212 | 10/1982 | Greene ................................ 623/21 |

FOREIGN PATENT DOCUMENTS 2445137  8/1980  France ................................. 623/20

Primary Examiner—Richard J. Apley
Assistant Examiner—James Prizant
Attorney, Agent, or Firm—Brumbaugh, Graves, Donohue & Raymond

[57] ABSTRACT

A wrist joint prosthesis comprises a metal radial component and a metal metacarpal component connected by a metal axle and providing triaxial motions that are comparable to those of the anatomical wrist joint and restraint of excessive motions. Energy is absorbed and shock loads are minimized by the interposition of a bearing member between the radial and metacarpal components and a bearing sleeve of polymeric material over the axle.

5 Claims, 14 Drawing Figures

WRIST JOINT PROSTHESIS

FIELD OF THE INVENTION

The present invention relates to a wrist joint prosthesis that provides for triaxial motions that are close to those of the anatomical wrist joint but also restrains excessive motions in a way that absorbs energy and minimizes shock loads at the limits of motion.

BACKGROUND OF THE INVENTION

Like other joints of the body, the wrist joint is subject to severe arthritis that produces great pain, considerable deformity and substantial loss of function. Although many efforts have been made to develop a satisfactory prosthesis for the wrist joint, none has to date come into widespread use.

One approach to the design of a wrist joint prosthesis involves a ball and socket connection between a radial component and a metacarpal component. This approach provides virtually no restraint on any motion of the prosthetic joint—all restraint must, therefore, come from the remaining soft tissues of the joint, and such restraint is likely to be considerably impaired in the severely diseased joint.

U.S. Pat. No. 4,229,841 granted Oct. 28, 1980, for "Wrist Prosthesis" describes and shows a two-axes prosthesis in which extension and flexion are afforded by a hinge or pivot pin connection having a latero-medially oriented axis and lateral angulation is provided by a second pivot pin oriented in the dorsal-volar direction substantially perpendicular to the latero-medial axis. No provision is made for axial rotation. It is not clear from the specification or drawings of this patent how much restraint, if any, there is on the permitted motions.

The inability of the prosthesis of U.S. Pat. No. 4,229,841 to provide axial rotation is believed to be an important deficiency, perhaps not so much because of diminishment of the function of the reconstructed wrist joint but, rather, because the prosthesis is required to carry all loads due to forces tending to produce axial rotation of the prosthetic joint. These loads, especially in cases where they are imposed by abruptly acting forces, can lead to loosening of the bone-cement-metal fixation structures of the prosthesis.

U.S. Pat. No. 4,229,841 describes other proposed wrist joint prostheses and certain deficiencies the patentees discern in them. Suffice it for the present inventors to state that they believe the prior art designs do not fully meet the requirements of restoring as much normal function as possible, of ensuring as much stability as possible through restraint on all motions and of having as high endurance as possible to minimize failures due to loss of adequate bone-cement-prosthesis attachment.

SUMMARY OF THE INVENTION

There is provided, in accordance with the present invention, a triaxial wrist joint prosthesis that affords motions of the wrist joint that closely duplicate those of the anatomical wrist joint, fully restrains excessive motions in all directions, and provides a high degree of absorption of the energy of loads imposed at the limits of all motions for improved durability. The prosthesis comprises a metal radial component having a stem that is adapted to be received in the distal portion of the radial medullary canal and secured therein by a cement and a plate-like portion adapted to reside at the distal end of the lower extremity of the radius. A boss extends distally from the plate-like portion at a location offset laterally outward (toward the ulna) from the axis of the radial stem. The boss has medial and lateral surfaces, a transverse hole that opens at those surfaces, and a spherical surface that extends along the volar, distal and dorsal aspects.

The prosthesis further comprises a metal metacarpal component having a generally U-shaped body portion composed of laterally spaced-apart legs that are adapted to straddle the boss of the radial component and a base interconnecting the legs. Stems extend distally from the base and are adapted to be received in the proximal portions of the second and third metacarpals and to be secured therein generally by a cement.

A metal axle extends between and is joined to the legs of the metacarpal component and passes through the hole in the boss of the radial component. A sleeve of polymeric material surrounds the portion of the axle within the hole and is in clearance with the hole in such a way as to afford constrained radio-ulnar angulation and axial rotation of the metacarpal component relative to the radial component. A generally U-shaped bearing component of a polymeric material is received within the U-shaped body portion of the metacarpal component. The bearing component has a spherical seat matching and engaging the spherical surface on the radial boss for the articulations and rotation of the prosthetic joint. The dorsal and volar aspects of the base of the bearing component are adapted to engage the dorsal and volar aspects of the plate-like portion of the radial component and in conjunction with engagement between the sleeve and the hole in the boss restrain extension and flexion of the metacarpal component to magnitudes corresponding substantially to those of the anatomical wrist joint. Arcuate proximal surfaces on the legs of the bearing component engage distal surfaces of the plate-like portion of the radial component on either side of the boss to restrain radio-ulnar angulation of the metacarpal component to magnitudes corresponding generally to those of the anatomical wrist joint.

In a preferred embodiment, the distal surfaces of the radial component that restrain radio-ulnar angulation are arcuate concavities, preferably tapered outwardly and proximally and thus of conical form, and have a common centerline that is spaced-apart a small distance distally from the centerline in the transverse hole in the boss of the radial component. With this geometry restraint of radioulnar angulation under compression is provided predominantly by engagements of the distal and proximal surfaces of the respective radial and bearing components and only secondarily by forced engagements between the hole in the radial boss and the sleeve, thereby significantly reducing the possibility of loosening the retention of the radial component due to forces acting on the radial boss.

The prosthesis allows free motion in all three axes and, therefore, restores full function, at least to the extent permitted by the soft tissues of the patient's wrist and hand. Excessive motions in all directions are, nonetheless, restrained. All transfers of forces between the components at the limits of all motions are from metal to plastic to metal. The inherent elasticity of the plastic absorbs the energy of contacts at the limits of motion and cushions what otherwise might be a sharp impact or shock load that could cause the bone-cement-metal fixation structures to loosen. Because the prosthesis allows motion in all directions, the soft tissues of the joint absorb some of the forces that would otherwise have to be taken by the prosthesis.

For a more complete understanding of the invention, reference may be made to the following description of an exemplary embodiment, taken in conjunction with the figures of the accompanying drawings.

DESCRIPTION OF THE DRAWINGS

The drawings illustrate the components of the embodiment, which is for the right wrist joint, by plan and elevational views taken from various aspects, as follows.

DESCRIPTION OF THE DRAWINGS

Figure 1:
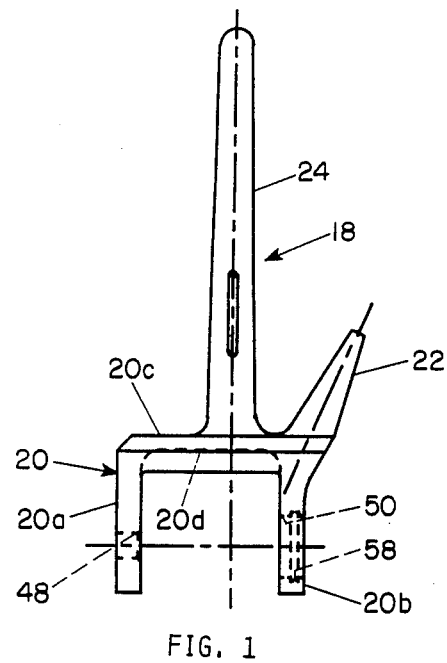
FIGS. 1, 2 and 3—the metacarpal component, bearing member and radial component, respectively, from the volar aspect.
Figure 4:
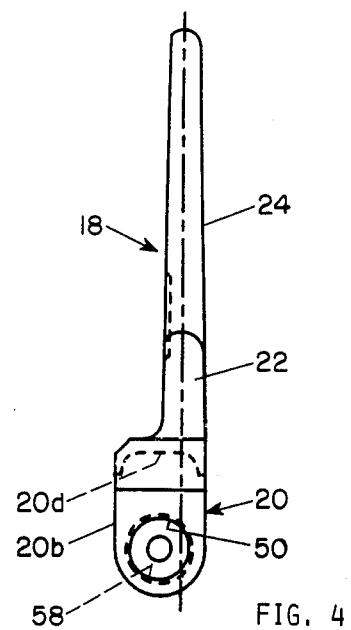
FIGS. 4, 5 and 6—the metacarpal component, bearing member and radial component, respectively, from the radial aspect.
Figure 2:
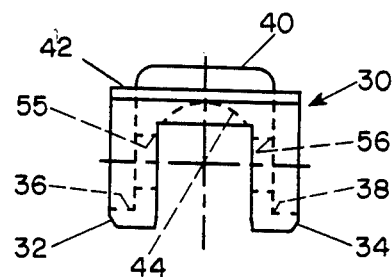
Figure 5:
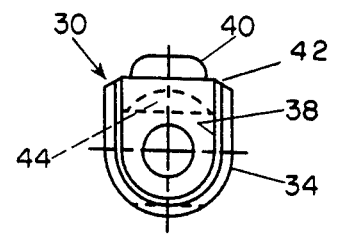
Figure 3:
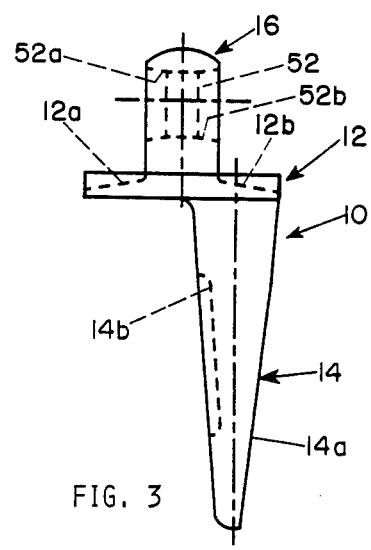

The prosthesis is intended to reduce pain as much as possible and restore shape and function to relatively severely diseased wrist joints. Generally, the bones of a severely diseased wrist joint are greatly eroded, and some of the carpals may have largely disappeared. The joint will often be considerably foreshortened. Whatever is left of the three medial carpals in each row is surgically removed to make room for the prosthesis, and the distal ends of the radius and ulna are cut away.

The radial component 10 of the prosthesis comprises a plate-like portion 12 that replaces the distal anatomical surface at the lower extremity of the radius, a stem 14 that tapers proximally from the portion 12 and joins the plate-like portion 12 at the radial edge (i.e., is offset in the radial direction from the center of the portion 12) and a boss 16 that extends distally from the center of the plate-like portion. The nominal plane of the plate-like portion lies oblique to the axis of the stem so that the distal surface faces a few degrees in the volar direction, relative to the stem. This nominal plane defines the limits of extension and flexion, so it is biased toward flexion, relative to the axis of the stem, in correspondence with the normal anatomical wrist joint.

The boss 16 defines the three axes of articulation of the prosthesis. As in the anatomical wrist joint, the axis of radio-ulnar deviation is offset laterally externally (toward the ulna) from the axis of the radius, and the axis of extension-flexion is offset in the volar direction from the radial axis. The stem 14 is received in the distal end of the medullary canal of the radius and is held in place by a surgical cement. Fixation is enhanced by a flat surface 14a on the radial aspect of the stem and a groove 14b on the ulnar aspect.

Figure 7:
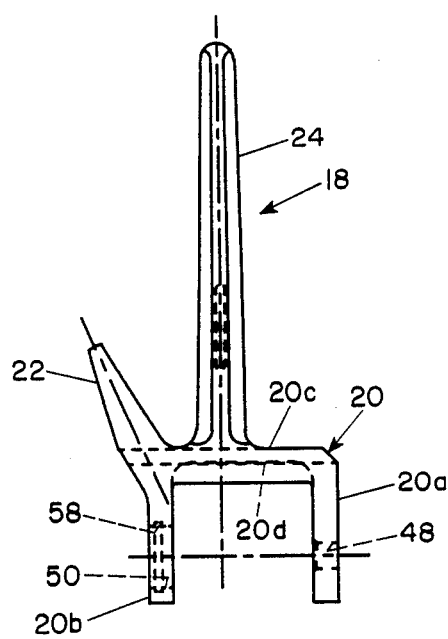
FIGS. 7 and 8—the metacarpal component from the dorsal and proximal aspects, respectively.
Figure 8:
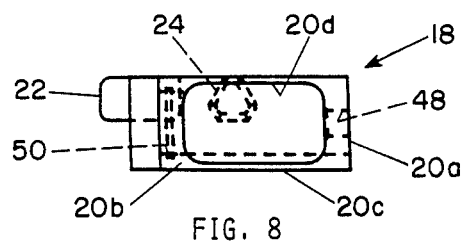
Figure 12:
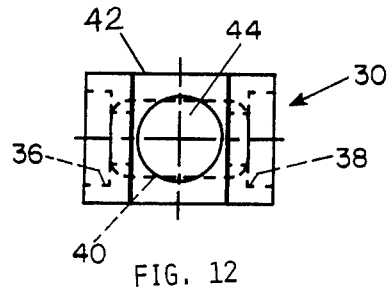
FIG. 12—the bearing component from the proximal aspect.
Figure 10:
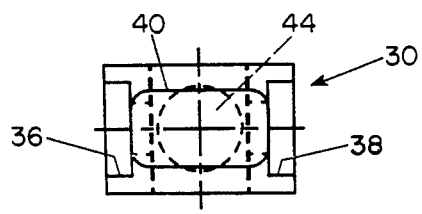
FIG. 10—the bearing component from the distal aspect.
Figure 11:
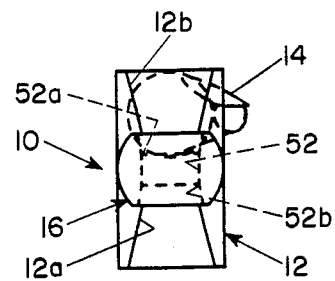
FIG. 11—the radial component from the distal aspect.
Figure 9:
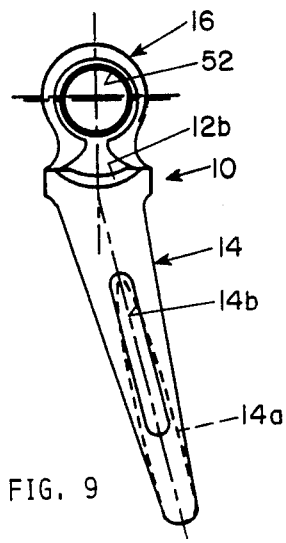
FIG. 9—the radial component from the ulnar aspect.

The metacarpal component 18 comprises a proximal body portion 20 that is generally U-shaped as viewed in the dorso-volar direction (FIGS. 1 and 7) and consists of a pair of laterally spaced-apart legs 20a and 20b that straddle the boss 16 in the assembled prosthesis and a base 20c joining the legs. Stems 22 and 24 extend distally from the base 20c and are cemented in place in the second and third metacarpals, respectively.

The U-shaped body portion 20 of the metacarpal component 18 receives a U-shaped bearing member 30 made of a rigid surgical-grade polymer, such as ultra high molecular weight polyethylene (UHMWPE). The legs 32 and 34 of the bearing member have notches 36 and 38 in their outer surfaces that receive the respective legs 20a and 20b of the metacarpal component, and a boss 40 on the distal surface of the base 42 of the bearing member nests in a complementarily-shaped recess 20d in the metacarpal base 20c. In the assembled prosthesis, the boss 16 of the radial component 10 is received between the legs 32 and 34 of the bearing member. The boss 16 has a spherical surface extending along its dorsal, distal and volar aspects that seats in a concave spherical seat 44 in the bearing member.

Figure 13:
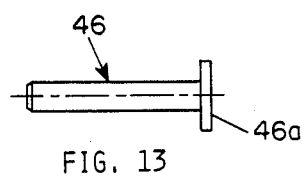
FIG. 13—the pin in elevation.
Figure 14:
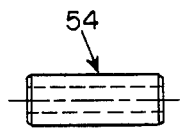
FIG. 14—the sleeve in elevation.

The components of the prosthesis are connected by a metal pin 46 (FIG. 13) that extends through holes 48 and 50 in the legs 20a and 20b of the metacarpal component 18 and a hole 52 in the boss 16 of the radial component 10. A sleeve 54 (FIG. 14) of a rigid surgical grade polymer, such as UHMWPE, fits over the pin 46 and into holes 55 and 56 in the legs 32 and 34 of the bearing member 30. The pin 46 has an enlarged head 46a that is stopped against the end of the sleeve 54 and is retained by a tiny C-ring (not shown) installed in a circumferential groove 58 in the wall of the hole 50.

The preferred material for the metal components of the prosthesis is Ti-6Al-4V, but other suitable materials can be used.

The prosthesis affords the following motions of the metacarpal component relative to the radial component:

Flexion-extension occurs by pivoting of the metacarpal component relative to the radial component about the axis of the pin 46 up to about 92° flexion and about 72° extension without restraint. The limits of free flexion-extension are established when the volar and dorsal aspects of the base portion of the bearing member 30 engage the volar and dorsal edges of the base portion 12 of the radial component. The sleeve 54 bears against the distal part of the wall of the hole 52 at both limits of flexure. The elasticity of the sleeve and the bearing member permits several degrees (of arc) of restrained flexion and extension beyond the limits of free flexure; the energy of the forces that produce the additional, restrained movement are absorbed by deformation of the plastic material of the sleeve and the bearing member.

Radio-ulnar deviation is permitted without restraint up to 4° in each direction from neutral by clearances between, first, the sleeve 54 and the hole 52 in the boss 16 and, second, the convexly arcuate proximal aspects of the legs 32 and 34 of the bearing member and the respective conical concavities 12a and 12b on the distal aspect of the carpal articular portion 12 of the radial component. Laterally outwardly divergent conical surfaces 52a and 52b at the ends of the hole 52 in the boss limit angulation of the sleeve in all directions. Engagement of the arcuate end surfaces of the bearing member legs 32 and 34 against the concavities 12a or 12b provide restraint of radio-ulnar deviation. Several degrees of restrained deviation beyond the limits of free deviation are permitted by deformation of the plastic elements, with energy absorption by such deformation. Deviation is restrained in all positions of flexion and extension and can occur until a few degrees from full flexion and extension.

Figure 6:
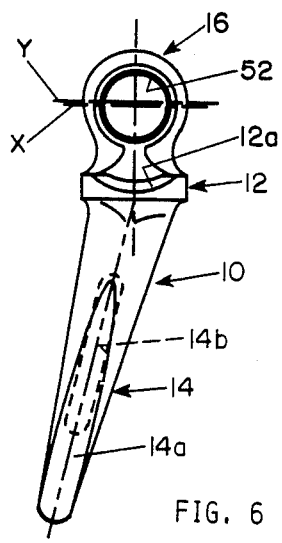

With the hand fully extended and without radioulnar deviation, compression loads are transmitted from the metacarpal component through the bearing member to the radial component at the region of contact between the spherical surface of the radial boss 16 and the matching spherical seat 44 of the bearing member. Upon radio-ulnar deviation in either direction, the arcuate surface of one or the other of the leg portions 32 and 34 of the bearing member 30 engages the corresponding concavity 12a or 12b of the base portion 12 of the radial component. Under the compression load, engagement between either of the legs 32 and 34 and the corresponding surface 12a or 12b will occur without the sleeve 54 engaging the companion conical surface 52a or 52b, inasmuch as the center axis X of the concavities 12a and 12b is offset a small distance proximally from the center axis Y of the conical surfaces 52a and 52b (see FIG. 6). Accordingly, the restraint of radio-ulnar deviation will often occur without forced engagement between the sleeve 54 and the conical surfaces in the radial boss 16, and the possibility of loosening of the retention of the radial component due to forces acting on the radial boss is significantly reduced.

Axial rotation of about 8° total without restraint and a few degrees beyond with restraint and energy absorption is permitted by the clearance between the sleeve 54 and the hole 52 throughout most of the full range of extension and flexion, the unrestrained limits of rotation being established by the cone angles of the conical surfaces 52a and 52b of the hole 52 in the radial boss 16.

There are slight laxities in all directions because of the lateral clearances between the boss and the respective legs of the bearing member and the radial clearance all around between the sleeve and the hole in the boss. The energy-absorption and cushioning effects of the metal-plastic-metal force transfers at the limits of the small translations permitted in all axes reduce the possibility of loss of retention of the prosthesis. The soft tissues of the joint absorb some of the forces that would have to be carried entirely by the prosthesis if there were no laxities.

The radial component and the metacarpal component are surgically implanted in the patient separately. After the bearing member is placed in its nested position on the metacarpal component, the sleeve 54 is then inserted through the large hole 50 in the leg 20b of the metacarpal component, followed by insertion of the pin 46 and installation of the C-ring (not shown) in the groove 58.

We claim:

1. A total wrist joint prosthesis comprising a metal radial component having a stem adapted to be received in the distal portion of the radial medullary canal and secured therein; a plate-like portion adapted to reside at the distal end of the residual anatomical radius, and a boss extending distally from the plate-like portion, the boss being offset from the axis of the stem in both the ulnar and volar directions, having a transverse hole and having a spherical surface along its volar, distal and dorsal aspects; a metal metacarpal component having a generally U-shaped body portion composed of laterally spaced-apart legs that are adapted to straddle the boss of the radial component and a base interconnecting the legs and having stems that extend distally from the base and are adapted to be received in the proximal portions of the second and third metacarpals and to be secured therein; a metal axle extending between and joined to the legs of the metacarpal component and passing through the hole in the boss of the radial component; a sleeve of polymeric material surrounding the portion of the axle within the hole, the sleeve being in clearance with the hole to afford constrained radio-ulnar angulation and axial rotation of the metacarpal component relative to the radial component; and a generally U-shaped bearing component of a polymeric material received proximally to the boss within the base portion of the metacarpal component, the bearing component having a spherical seat matching and engageable by the spherical surface of the radial boss for flexural articulation of the prosthetic joint and having dorsal and volar surfaces adapted to engage the dorsal and volar aspects of the plate-like portion of the radial component and in conjunction with engagements between the sleeve and the hole in the boss restrain extension and flexion of the metacarpal component to magnitudes corresponding substantially to those of an anatomical wrist joint, and having convexly curved proximal surfaces that are adapted to engage distal surfaces of the plate-like portion of the radial component on either side of the boss to restrain radio-ulnar angulation of the metacarpal component to a magnitude corresponding substantially to those of the anatomical wrist joint.

2. A wrist joint prosthesis according to claim 1 wherein the hole in the boss of the radial component includes conical portions that taper outwardly from the medial to the lateral adjacent each lateral aspect of the boss, thereby to afford radio-ulnar angulation and axial rotation of the prosthetic joint.

3. A wrist joint prosthesis according to claim 1 wherein the each distal surface of the plate-like portion is a concavity which is adapted to be engaged by a corresponding one of the convexly curved proximal surfaces of the bearing component to restrain radio-ulnar angulation throughout a substantial range of flexion and extension.

4. A wrist joint prosthesis according to claim 3 wherein each of the concavities slopes laterally and proximally away from the boss at an angle corresponding to the limit of radio-ulnar angulation.

5. A wrist joint prosthesis according to claim 3 or claim 4, wherein the distal surfaces of the radial component are arcuate and have a common centerline of curvature, which centerline is spaced apart a small distance distally from the centerline of the transverse hole in the boss of the radial component so that restraint of radio-ulnar angulation under compression is provided predominantly by engagement of said distal and proximal surfaces of the respective radial and bearing components and only secondarily by engagement between the sleeve and the hole in the boss.

* * * * *